United States Patent [19]

Goble et al.

[11] Patent Number: 4,738,255
[45] Date of Patent: Apr. 19, 1988

[54] SUTURE ANCHOR SYSTEM

[75] Inventors: E. Marlowe Goble, Logan, Utah; Larry DeHart, Placentia, Calif.

[73] Assignee: Biotron Labs, Inc., Brea, Calif.

[21] Appl. No.: 848,929

[22] Filed: Apr. 7, 1986

[51] Int. Cl.$^4$ .............................. A61F 1/00; A61F 5/04
[52] U.S. Cl. ........................ 128/92 YF; 128/92 VD; 128/330; 128/334 C; 128/335.5; 623/13; 623/16; 227/DIG. 1; 408/159; 411/55; 72/391
[58] Field of Search ............... 128/330, 335.5, 335, 128/334 C, 334 R, 305, 92 V, 92 VD, 92 YF, 92 YE, 92 YD, 92 YC, 92 YW, 92 YR; 24/150 FP, 156 R, 155 R; 227/DIG. 1, 120; 408/159, 180; 411/54, 55, 57, 60, 340, 345, 346, 344; 623/13, 16; 72/391, 453.17

[56] References Cited

U.S. PATENT DOCUMENTS

| 887,074 | 5/1908 | DePage | 128/92 YF X |
|---|---|---|---|
| 2,562,419 | 7/1951 | Ferris | 128/92 V |
| 2,665,597 | 1/1954 | Hill | 411/55 X |
| 3,775,825 | 12/1973 | Wood et al. | 128/334 C X |
| 3,883,901 | 5/1975 | Coquard et al. | 128/92 YF X |
| 4,011,602 | 3/1977 | Rybicki et al. | 128/92 YF X |
| 4,091,880 | 5/1978 | Foltz et al. | 128/92 VT X |
| 4,136,547 | 1/1979 | Ewig, Jr. et al. | 72/391 |
| 4,140,111 | 2/1979 | Morrill | 128/92 V |
| 4,141,087 | 2/1979 | Shalaby et al. | 128/92 YF X |
| 4,244,370 | 1/1981 | Furlon et al. | 128/303 R |
| 4,287,807 | 9/1981 | Pacharis et al. | 411/55 X |
| 4,307,636 | 12/1981 | Lacey | 408/159 X |
| 4,337,773 | 7/1982 | Raftopoulos et al. | 128/303 R X |
| 4,347,768 | 9/1982 | Boehm | 408/180 X |
| 4,383,527 | 5/1983 | Asnis et al. | 128/92 V X |
| 4,409,974 | 10/1983 | Freedland | 128/92 YF X |
| 4,414,967 | 11/1983 | Shapiro | 128/92 YF X |
| 4,425,782 | 1/1984 | Todisco | 72/391 |
| 4,529,022 | 7/1985 | Jacobson | 408/159 X |
| 4,570,624 | 2/1986 | Wu | 128/92 VD |
| 4,590,928 | 5/1986 | Hunt et al. | 623/13 X |
| 4,630,510 | 12/1986 | Belanger | 72/391 X |
| 4,632,100 | 12/1986 | Somers et al. | 128/330 X |
| 4,649,732 | 3/1987 | Molina | 72/391 |

FOREIGN PATENT DOCUMENTS 0644468 of 1979 U.S.S.R. .......................... 128/92 V

Primary Examiner—Richard J. Apley
Assistant Examiner—David Bender
Attorney, Agent, or Firm—M. Reid Russell

[57] ABSTRACT

A suture anchor system that includes a drill for turning into a bone mass with sissoring blades pivotally connected in a longitudinal drill shaft slot proximate to a cutting end thereof, the blade ends to sissor to extend cutting edges outwardly therefrom, which sissoring occurs at a certain depth of penetration into the bone mass, cutting a flared or skirted hole therein, to receive a suture anchor whereto a suture is secured. The suture anchor consists of a suture rivet and slotted ring and is formed by moving the suture rivet into the slotted ring, that ring breaking at spaced apart slots formed therein and flaring into a skirt, the anchor rivet and slotted ring thereby locked together as the suture anchor, which suture anchor has approximately the same shape but a slightly lessor diameter than the hole formed in the bone mass. The suture rivet and slotted ring are mounted on an applicator for fitting into the bone mass hole, the applicator consisting of a grip and trigger pivotally coupled thereto, such that, with trigger movement towards that grip a plunger attached thereto will be moved also, which plunger is releasably secured to a head of a mandrel that is telescoped through an ejector that is for releasable mounting in the applicator, which mandrel slides in the ejector and connects on its distal end to the suture rivet. Plunger travel therefor, responsive to trigger depression, moves the mandrel to pull the suture anchor into the slotted ring and the mandrel thereafter separates from the suture anchor allowing the applicator to be removed from the seated suture anchor and expose the suture attached thereto.

41 Claims, 4 Drawing Sheets

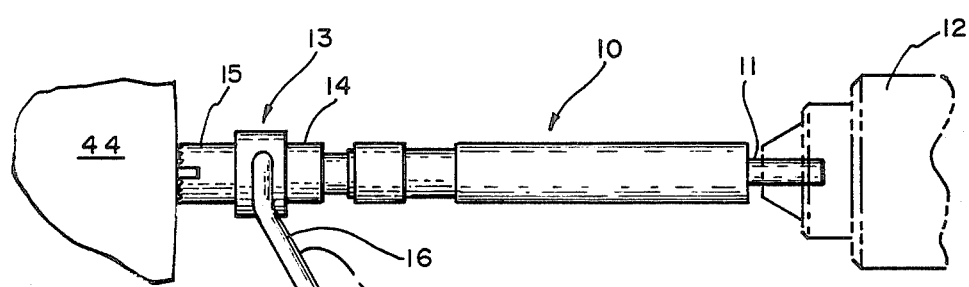
FIG. 1
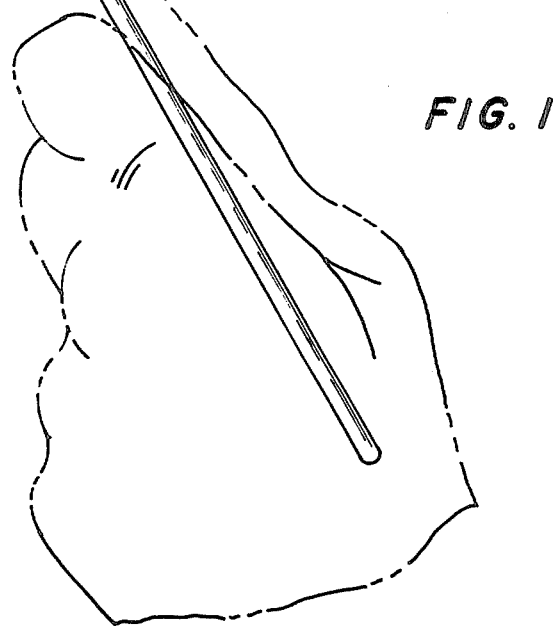
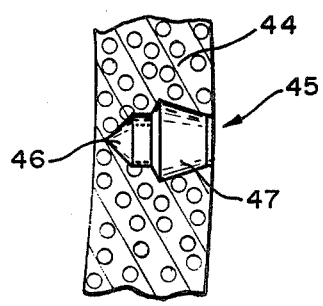
FIG. 7
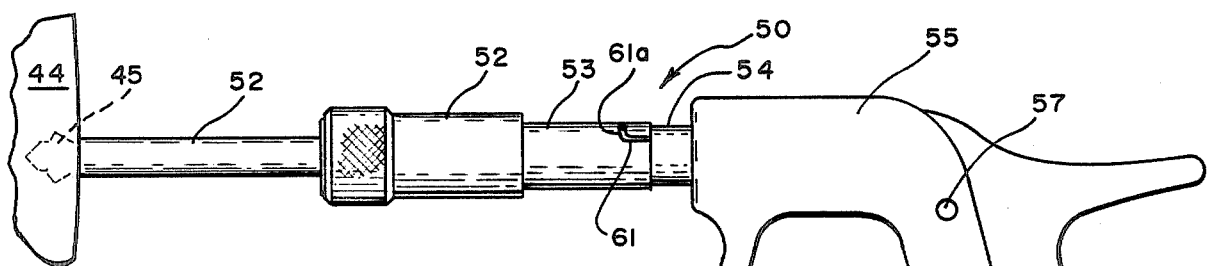
FIG. 8
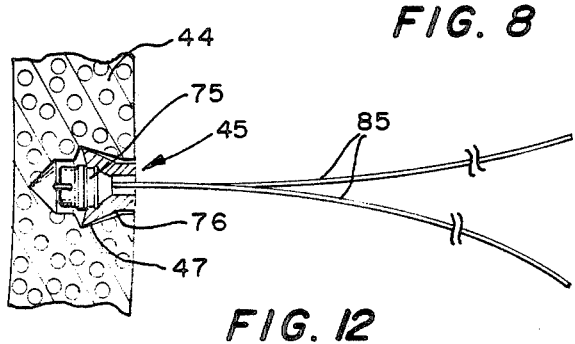
FIG. 12

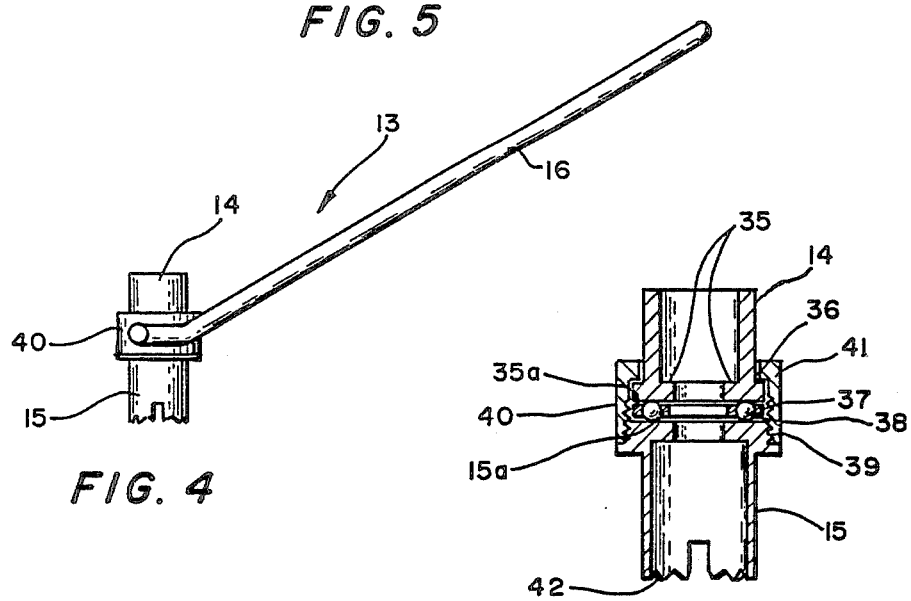
FIG. 5
FIG. 4
FIG. 6
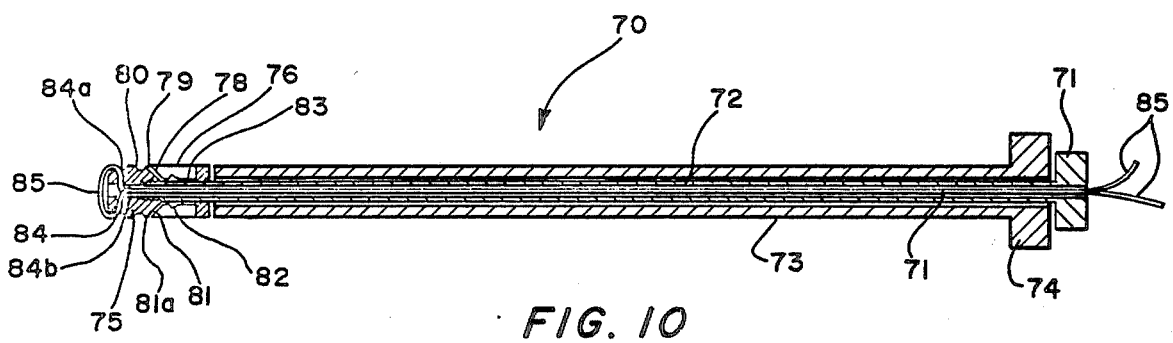
FIG. 10
FIG. 11

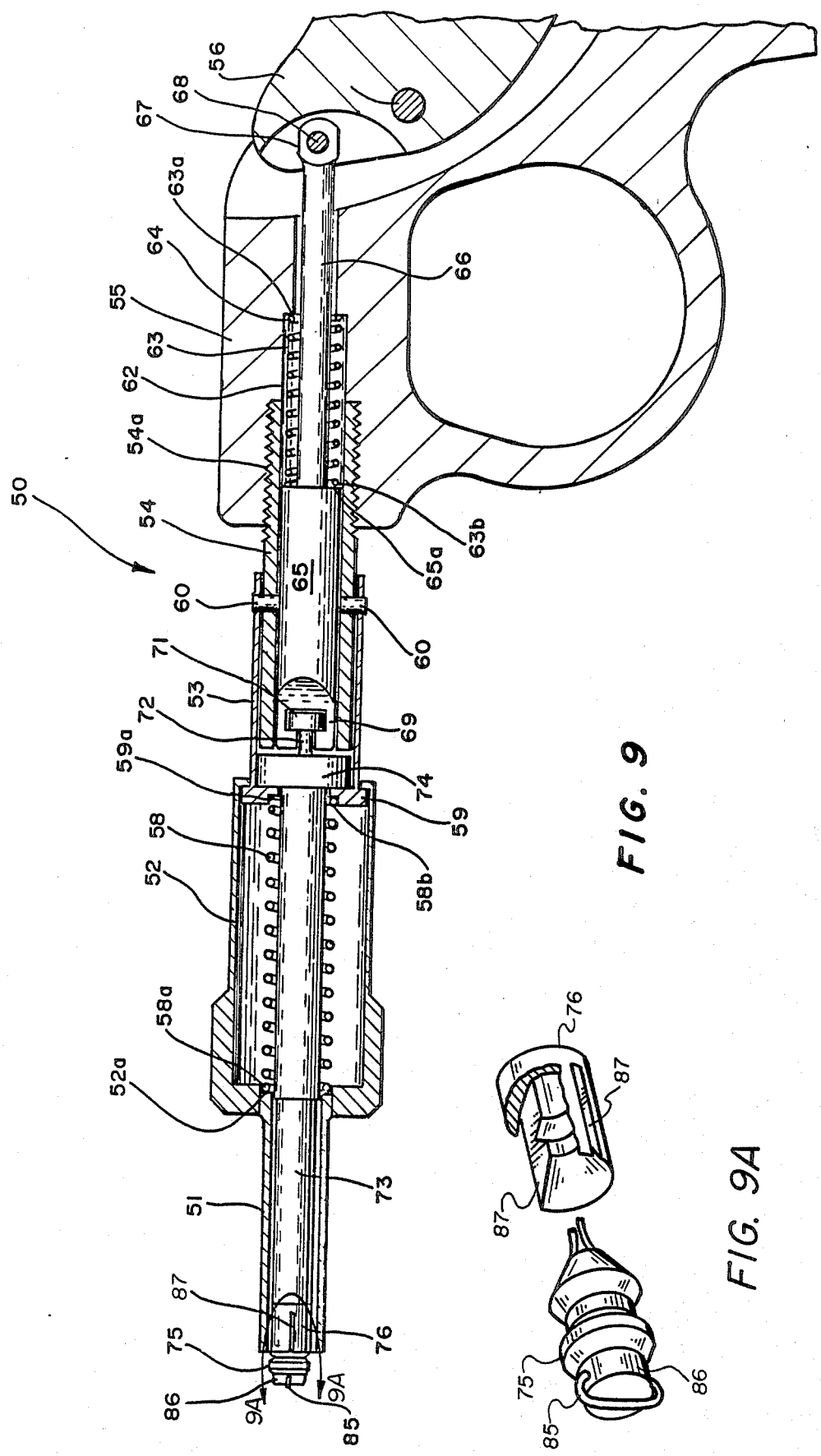

SUTURE ANCHOR SYSTEM

BACKGROUND OF THE INVENTION

1. Field Of The Invention

This invention relates to appliances for use during certain orthopaedic surgical procedures, particularly those procedures involving replacing or securing a suture to a bone mass, as for example, to attach and maintain a ligament thereto.

2. Prior Art

In a practice of certain orthopaedic surgical procedures, particularly those involving attachment of a ligament to a bone mass, as for example, knee or elbow surgery, it has long been a problem to effectively anchor that ligament to the bone mass surface during the healing process. Which healing process involves the ligament growing to that bone mass to restore mobility to the orthopaedic patient. The problem of locating and securing a suture to a bone mass was addressed in an earlier currently pending patent application by one of the inventors, E. Marlowe Goble entitled "Suture Anchor Assembly" U.S. Pat. No. 4,632,100. This patent application involves a combination drill and anchor appliance formed from stainless steel or like non-corrosive metal. The suture anchor includes threads formed around one end and a fluted drill on the distal end therefrom. The appliance, in a single step, with a separate drill, is turned into the bone mass, the threads formed around the upper end portion thereof turned into that bone mass. Removal of the drill from the suture anchor exposes a suture that is secured in the anchor head or top surface. This appliance is particularly effective for securing a suture to a bone at a point thereon where access to that bone surface is tight or is in a constricted area of the body. When the suture anchor is secured in the bone mass, it will remain therein for the life of the patient or until it is removed. While this generally will not be a problem, in certain circumstances it is desirable to provide an appliance that will be bio-degradable within the body such that, after a period of time, it and the suture will be dissolved. Prior to the body absorbing the anchor and suture the ligament will have grown onto the bone area where the suture anchor was located. The present invention provides both a drilling device and a suture anchor applicator that are operated in separate steps in the process for securing a suture anchor to a bone mass that may be bio-degradable to be dissolved by the body after the healing processes have taken place.

The above cited earlier patent application in a suture anchor assembly sets out certain earlier orthopaedic devices. These arrangements include patents by Furlow et al., U.S. Pat. No. 4,244,370 and Asnis, et al., U.S. Pat. No. 4,383,527 that describe, respectively, a device for positioning an implant within the soft body tissue and a drill guide for guiding guide pins drilled into bone mass. Neither of these devices however, involves a drill, suture anchor applicator, or suture anchor like those of the present invention. Additionally, the earlier suture anchor assembly patent application also cites patents by Morrill, U.S. Pat. No. 4,140,111, Troutner, et al., U.S. Pat. No. 4,091,880, and Raftopoulous, et al., U.S. Pat. No. 4,337,773 that all involve drill arrangements. The drill arrangement of the present invention is, however distinct therefrom in that it provides a fluted drill wherefrom sissoring sections will strategically extend outwardly to cut a flared hole within a bone mass.

SUMMARY OF THE INVENTION

It is therefore, a general object of the present invention to provide a suture anchor system that includes a drill and guide arrangement for drilling a opening or hole into a bone mass that will internally be outwardly flared to accomodate a suture anchor dispensed from an applicator, which suture anchor in that insertion will be expanded appropriately within that drilled hole and has a suture connected thereto.

Another object of the present invention is to provide a guide to be held by a surgeon operator and positioned on a bone mass whereat a suture is to be anchored, which guide receives a drill of the present invention inserted therethrough, the guide arranged to initiate at a certain depth of drill penetration into the bone mass, operation of sissoring blades of that drill that will then cut an outwardly tapered hole portion below the bone mass surface, the sissoring blade portion to retract when the drill is withdrawn.

Another object of the present invention is to provide an anchor applicator for use by the surgeon operator who, after appropriate suction and removal of excess tissue from the formed hole, inserts an anchor rivet and slotted ring mounted on a barrel end of the applicator into the formed hole and operates a trigger portion thereof to move the anchor rivet into that slotted ring forming a suture anchor that is thereby permanently set in that hole, the suture anchor including a suture secured thereto that is freed when the applicator is removed and can then be used in a surgical procedure.

Still another object of the present invention is to provide as the anchor assembly, an anchor rivet and slotted ring that by operation of the applicator trigger are pulled and locked together as a suture anchor, the anchor rivet and slotted ring formed from a bio-degradable material that, when installed within bone mass, after healing will be absorbed along with the suture by the body.

Still another object of the present invention is to provide a suture anchor system comprising a drill and guide arrangement and a suture anchor seating arrangement therefor as components for use by a surgeon operator performing an orthopaedic procedure to set and secure a reliable suture anchor within a bone mass, the suture anchor to resist withdrawal therefrom such that, with an application of an increasing tensil stress to that suture, the suture will break before the anchor will be dislodged.

Still another object of the present invention is to provide a suture anchor system for use in a two step surgical procedure to safely and quickly secure a suture to extend from a point on a bone mass that can be used to attach a ligament thereto, or the like.

In accordance with the above objects, the present invention in a suture anchor system includes a drill preferably for mounting in a chuck of a conventional air drill and in a manually operated suture anchor applicator. The drill includes, on one end thereof, a stem for securing in a chuck of the conventional air drill. The drill shaft is continuous ending in a fluted drill end, the shaft extending through and has a first or spring housing connected thereto wherein a coil spring is arranged. The coil spring is compressed between a spring stop arranged within the spring housing and an upper guide sleeve that is telescoped therein. The upper guide sleeve will travel into the spring housing, compressing the coil spring. The upper guide sleeve, in turn, includes an open collar end distal from the spring engaging end thereof that receives a second or lower guide sleeve telescoped therein. The respective upper and lower guide sleeves are secured together at that collar by turning of set screws through the collar against a groove formed around the lower sleeve, forming a single guide sleeve.

The fluted drill end, above the pointed end thereof is slotted to contain sissoring blades journaled thereacross. The sissoring blades individually consist of a tapered cutting edge on one end thereof, a slide or ramp portion that is outset from the blade, above the pivot coupling, and ends in a stop on the distal end to the cutting edge. The blades are pivot coupled so that the slide or ramp portions of each face oppositely, the lower guide sleeve to travel thereon above the sissor pivot. So arranged, with guide sleeve travel into the spring housing, against the spring biasing, the lower guide sleeve will travel along blade sloping side portions, to move those blade slide portions together to sissor apart or flare outwardly the blade cutting edges. The blade cutting edges are sharpened appropriately such that, when flared outwardly, will form a skirt to that fluted end that will cut into the bone mass, forming a hole that tapers to a greater diameter within the bone mass from a lesser diameter hole at the point of entry.

Control of sissoring blade pivoting is provided by travel of the lower guide sleeve against the coil spring biasing. That control is provided by a guide wherethrough the drill is turned into a bone mass. At a certain depth of travel of the drill fluted end into the bone mass, a collar or step surface in the guide will engage the end of lower guide sleeve. With further travel of the drill fluted end into the bone mass the lower guide sleeve will be urged against the coil spring biasing, traveling along the sissor blades sloping slide or ramp portions, extending the blade cutting edges that cut an outwardly flared or skirt into that bone mass. During drill withdrawal, pressure on the lower guide sleeve at the guide collar is released, the lower guide sleeve thereby urged by the coil spring back into its original attitude, closing the sissoring blades together. The drill is thereby returned to its original diameter as it is withdrawn.

Thereafter, with removal of the bone chips, fragments and tissue from the hole, that hole is prepared to receive a suture anchor installed therein. To install the suture anchor, the present invention provides a manually operated applicator. The applicator consists of a handle section that includes a trigger that is pivotally connected thereto to be operated by the palm area of a surgeon operator's hand gripping that handle section. Closing of the trigger against the grip moves a plunger rearwardly in the handle section against the biasing of a plunger spring that is located in the grip coiled around the plunger. The plunger extends through the grip and terminates in a yoke secured across its end. The moving of the trigger against the grip moves that plunger and the yoke against the biasing of the plunger spring. The plunger is arranged to slide longitudinally within a plunger sleeve that is secured to the grip and receives a plunger housing telescoped thereover. An applicator barrel that includes a spring supported longitudinally in a spring housing arranged for telescoping attachment with the plunger housing.

The applicator assembly is arranged to open between the plunger yoke to the barrel open end. An anchor ejector is provided for telescope installation within the applicator barrel, a mandrel head end of that applicator to releasably fit into the plunger yoke to travel therewith. In assembling the applicator the barrel is telescoped over a collar end of the plunger housing. So arranged, the barrel spring with the ejector therein biases the applicator barrel away from the plunger housing. The applicator barrel can thereby be recessed into the plunger housing to expose an end of the anchor ejector.

The anchor ejector consists of an ejector sleeve that is open centrally from end to end and terminates in a collar on one end for fitting in the plunger housing. The ejector sleeve has a mandrel telescoped therethrough that includes the mandrel head on the one end thereof that is fitted into the plunger yoke, which mandrel is open longitudinally to receive a suture fitted therethrough and mounts a slotted ring sleeve followed by an anchor rivet across the other end. The suture connects to the anchor rivet such that, when the trigger is operated appropriately the anchor rivet will travel into and lock to the slotted ring that is expanded by that anchor rivet entry, the anchor rivet breaking off from the mandrel that is then pulled away leaving the suture extending from the combined anchor rivet and slotted ring.

As set out above, the barrel attached to the plunger housing is detachable from the plunger sleeve. This is accomplished by turning of a locking collar arrangement. This separation exposes the plunger yoke to allow a mandrel head of an anchor ejector to be fitted thereto. So arranged, plunger rearward motion that occurs when the trigger is depressed pulls the mandrel head therewith. The mandrel, in turn, moves within the ejector to pull the anchor rivet into the slotted ring. The ring is cut or pre-stressed at slots to break and flare outwardly, permitting the anchor to travel therein. The anchor includes an encircling ridge that is arranged to fit within a slot formed around the ring interior, that union providing a permanent coupling of the anchor rivet and slotted ring to form the suture anchor.

In practice, a surgeon holding the applicator inserts the anchor rivet and ring into the formed hole, the barrel end pushed back from the hole against the barrel spring biasing. Before they join together, the anchor rivet and ring are of a diameter to easily fit into the bone mass hole. With the ring broken by entry of the anchor rivet it is outwardly flared, as described above, to fit snuggly in the skirted portion of the hole drilled into the bone mass. Movement of the anchor rivet into the slotted ring and a subsequent pulling of the applicator from the seated suture anchor breaks the anchor rivet off from the mandrel end. The suture attached to the anchor rivet is then pulled out of the mandrel as the applicator is removed. The anchor rivet and slotted ring, when fitted together provide a positive locking together that is stronger in tension than is the suture.

After installation the suture attached to the seated suture anchor is tugged to make sure that the suture anchor is set in place. The suture can then be used to attach a ligament or the like to the bone mass. In practice, the anchor rivet and slotted ring are preferably manufactured separately from a bio-degradable material such as a polylactic acid plastic that will be dissolved and be absorbed by the body after a time period. Whereafter, the bone will grow into that area filling the hole as if there had never been a suture anchor installed therein.

THE DRAWINGS

In the drawings is shown that is presently regarded as the best mode for carrying out the invention.

FIG. 1 is a side elevation view of a surgeon operator holding a stationary end of a guide against a point on a bone mass and showing the drill of the invention mounted within a chuck and fitted through that guide to drill into that bone mass;

FIG. 4 is a side elevation view of the guide of FIG. 1;

FIG. 5 is a top plan view of the guide of FIG. 4;

FIG. 6 is a longitudinal sectional view taken along the line 6—6 of FIG. 5 showing the guide interior;

FIG. 7 is a sectional view of a section of bone showing a hole formed therein by operation of the drill and guide of FIG. 1;

FIG. 8 is a profile view of an anchor applicator of the present invention showing a grip and trigger on one end with a barrel extending therefrom that terminates in a narrow barrel portion on the opposite end;

FIG. 9 is a profile sectional view of the anchor applicator of FIG. 8 showing a plunger portion thereof connected to a trigger on one end mounting a yoke on the other plunger end, which yoke is shown fitted to a head of a mandrel that is telescoped into an ejector that is for installation through a lower barrel portion, which mandrel terminates in a slotted ring and an acorn shaped anchor rivet;

Figure 2:
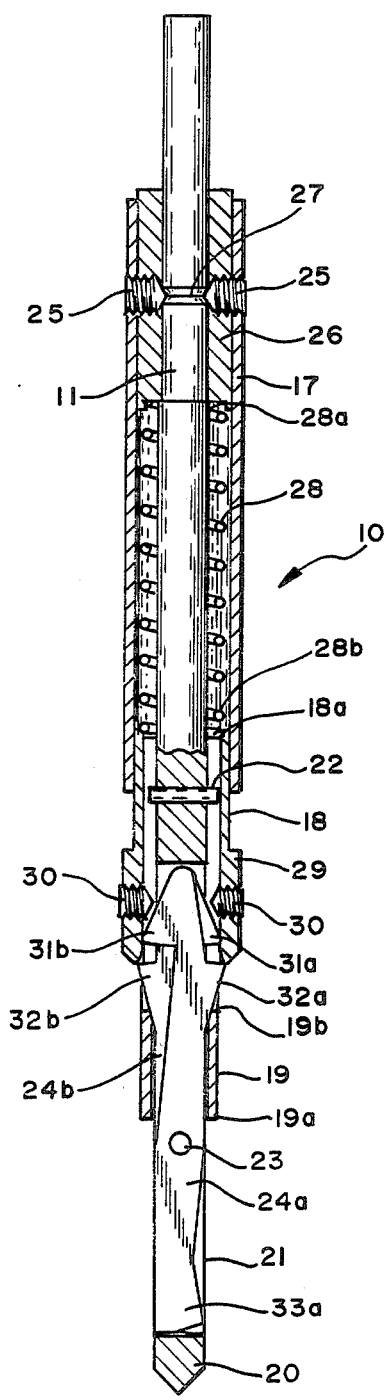
FIG. 2 is an expanded longitudinal sectional view of the drill of FIG. 1 shown removed from the guide and chuck, the drill shown as including a shaft that includes sissoring blade portions that are shown in a recessed attitude.

FIG. 9A, an exploded perspective view taken within the line 9A—9A of FIG. 9 showing the anchor rivet and slotted ring enlarged and separated from the applicator end;

FIG. 10 is a cross sectional view of the ejector of FIG. 9 showing the mandrel is open longitudinally and is telescoped longitudinally through an ejector sleeve, the slotted ring and anchor rivet fitted across the opposite ejector sleeve end, with a suture shown connected to the anchor rivet extending through that mandrel;

FIG. 11 shows a view like that of FIG. 10 only showing the mandrel head having been moved rearwardly pulling the anchor rivet into the slotted ring that has flared outwardly, the anchor rivet shown as having broken off from the mandrel end, the suture shown being pulled out of the mandrel; and FIG. 12 shows the section of bone with a hole formed therein of FIG. 6 with the suture anchor formed by the coupling of the anchor rivet and slotted ring fitted therein.

DETAILED DESCRIPTION

Referring Now to the Drawings

Figure 3:
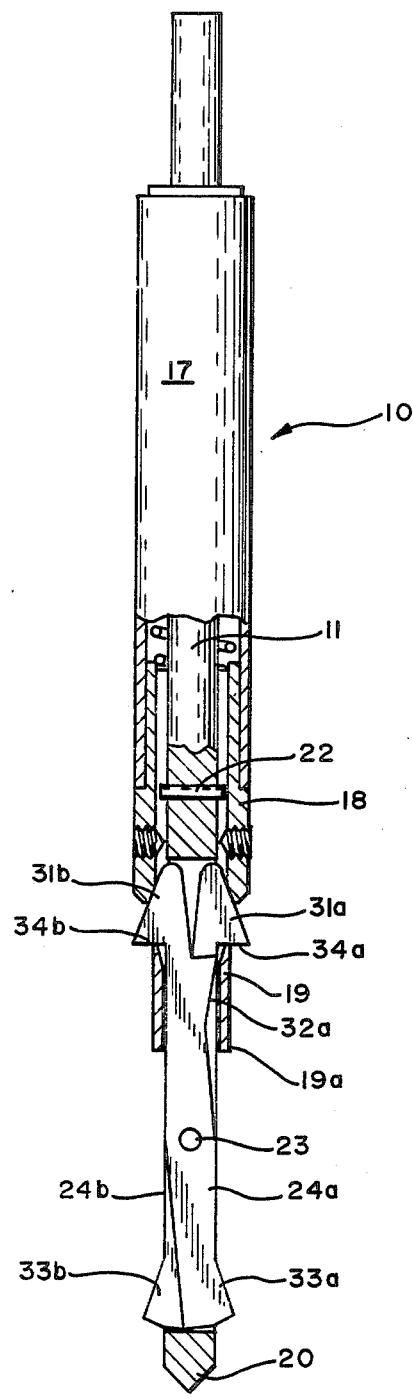
FIG. 3 is a view like FIG. 2 except that certain portions of the spring housing and drill shaft have been restored and showing the sissoring blades as having been sissored apart forming a skirted portion to the drill pointed end.

FIG. 1 illustrates a use of a drill 10 of the present invention for forming a hole in a bone mass. The drill includes a drill stem end of a drill shaft 11 that is for installation in a chuck 12 of a conventional air or electrically driven turning device or drill. The drill shaft 11 is continuous through the drill terminating in a fluted drill end 20, as shown in FIGS. 2 and 3. In FIG. 1 the drill 10 is shown fitted through a guide 13 that is further shown in FIGS. 4, 5, and 6 and will be described in detail later herein. The guide includes a turning sleeve 14 and a stationary sleeve 15. The assembly is maintained by a surgeon holding a handle 16 as shown in broken lines in FIG. 1, while he uses his other hand to operate an air driven drill to turn chuck 12. While not shown, it should be understood that the guide 13 could be connected to the drill and made a part thereof as by connecting a guide stationary portion through a spider and slide arrangement, not shown, the guide then including a turning portion like turning sleeve 14 that would contact the bone mass surface to function like the described stationary sleeve 15, remaining stationary on the bone mass as the drill and connected guide turn. So arranged, such spider and slide arrangement would allow the drill body to move back and forth in the guide, while the assembly is being turned by the drill. In the preferred embodiment, however, the stationary sleeve 15 is stationary on the bone mass while the turning sleeve 14 turns with the drill 10.

Shown in FIGS. 2 and 3 the drill shaft 11 from the stem extends through a spring housing 17, an upper guide sleeve 18, a lower guide sleeve 19, and terminates in a pointed fluted end 20. Drill shaft 11 from above the fluted end 20 is slotted longitudinally at 21 to below a guide pin 22, which guide pin 22 guides longitudinal travel of the upper guide sleeve 18 during travel thereof, as will be discussed in detail later herein. The slot 21 is to accomodate a sissor pivot 23 fitted laterally therethrough whereon are journaled sissor blades 24a and 24b within the slot 21. Shown best in FIG. 2 the spring housing 17 is coupled to the drill shaft 11 by set screws 25 that are turned through the spring housing and a spring stop 26 telescoped therein and engage a groove 27 formed around drill shaft. So arranged, the drill shaft is fitted through the spring housing and a coil spring 28 arranged therein, the assembly to turn with drill shaft 11. Coil spring 28 at an end 28a thereof rests against the spring stop 26 with its opposite spring end 28b engaging a dished or outwardly flared portion 18a of the upper guide sleeve. So arranged, the coiled spring biases that upper guide sleeve out of the spring housing 17. The upper and lower guide sleeves 18 and 19, respectively, are secured together by set screws 30 that are fitted through a collar 29 of that upper guide sleeve to engage the lower guide sleeve 19. The guide pin 22 extends through the drill shaft 11 to travel in slots formed within the upper guide sleeve to restrain rotation while allowing back and forth travel of that guide sleeve on the drill shaft.

The upper guide sleeve includes the collar portion 29, shown in FIGS. 2 and 3, wherein are arranged the set screws 30 that maintain the upper and lower guide sleeves 18 and 19 locked together. Lower guide sleeve 19 thereby moves the upper guide sleeve 18 therewith and is provided for opening and closing sissoring blades 24a and 24b. Shown in FIG. 2, the blades 24a and 24b are pivotally connected at sissor pivot 23 and include, on upper ends thereof adjacent to set screws 30, stops 31a and 31b. Intermediate from those stops to sissor pivot 23 are formed outwardly sloping slides or ramps 32a and 32b that extend from each blade. Slides or ramps 32a and 32b provide oppositely facing outwardly sloping surfaces, each to engage the interior of the lower guide sleeve. The lower guide sleeve rides on these slides or ramps from a lesser thickness up the ramp to a greater thickness of each blade to move the blade ends together.

FIG. 2 shows the guide sleeve at an initial attitude that it occupies prior to travel of the lower guide sleeve up slides or ramps 31a and 31b, in which attitude the lower end 19a thereof is proximate to the sleeve pivot 23 and the blades 24a and 24b are inset in slot 21. The lower guide sleeve is oppositely slotted to accomodate blade slides or ramps 32a and 32b and stops 31a and 31b travel therethrough. Prior to guide sleeve movement, a lower end 19b of the slot rests at approximately the bottom of each ramp 32a and 32b, in which attitude the opposite blade ends, blade cutting edges 33a and 33b, are recessed in the drill shaft slot to approximately the circumference of that drill shaft. Thereafter, as illustrated in FIG. 3, with the lower guide sleeve elevated to the attitude shown therein, the lower guide sleeve will have traveled up the slides or ramps 32a and 32b respectively, closing the blades together and moving the stops 31a and 31b outwardly to extend out from the drill shaft. So arranged, the flat faces 34a and 34b of those stops will block further vertical travel of the lower guide sleeve whereat the blades 24a and 24b will have pivoted around the sissor pivot 23 to where the blade cutting edges 33a and 33b are fully extended. In which extended attitude the cutting surfaces of the blade cutting edges 33a and 33b are faced opposite to the direction of drill shaft turning.

In the attitude shown in FIG. 3, the blade cutting edges 33a and 33b have been fully extended to form a skirt above the fluted drill end 20. This blade extension occurs during travel of the drill 10 into a bone mass and is controlled by travel of the lower guide sleeve 19 up slides or ramps 32a and 32b to where the lower ends 19b of the guide sleeve slot contact the blade stop flat faces 34a and 34b. In operation, this lower sleeve travel is initiated by contact of the lower guide sleeve end 19a with a step 35 that is formed within the turning section 14 of the guide 13, as shown best in FIGS. 5 and 6. After initial contact of the lower guide sleeve with the guide stop, as the drill fluted end 20 travels further into the bone mass, that lower guide sleeve is further moved against the biasing of coil spring 28, and the blade cutting edges 33a and 33b are extended outwardly to a skirt. This blade cutting edge extension takes place after the drill has passed into the bone mass, the extended edges thereby cutting a hole that has a greater diameter within the bone mass than the hole has at its point of entry on the bone mass surface. While the arrangement of blade cutting edges 33a and 33b for cutting the skirt shape of the hole, as shown in FIG. 12, is preferred, it should be understood that another blade edge configuration that would form a different shape of hole configuration could be employed within the scope of this disclosure. Such shape would, however, have to be such as to accomodate the suture anchor installed therein and the interior diameter of such hole should be greater than that of the hole entry at the bone mass surface.

As set out above, the extension of the blade cutting edges 33a and 33b, as illustrated in FIG. 3, is provided by travel of the lower guide sleeve up blade slides or ramps 32a and 32b. Upon release of the pressure or force exerted on the drill that urges the lower guide sleeve 19 against the collar or step 35, as in withdrawal of the drill from guide 13, the biasing of spring 28 will move that lower guide sleeve back to the attitude shown in FIG. 2 whereat the blade cutting edges 33a and 33b are drawn back into the drill shaft.

The guide 13 shown in use in FIG. 1 is further illustrated in the FIGS. 4, 5, and 6 to include the described turning portion 14 and stationary portion 15 and handle 16 that is held by a surgeon operator. As set out above, step 35 is provided within the guide turning portion for engaging the lower end 19a of the lower guide sleeve 19. Shown best in FIGS. 6, the step 35 is part of the rotating sleeve 14 that is also flared outwardly into collar 36. A turning sleeve 14 under surface 35a of the step 35 and collar 36 rest on a bearing 37 that contains, preferably, ball bearings 38. The bearing 37 separates the turning sleeve from the upper end 15a of the stationary sleeve 15. The stationary sleeve further includes threads 39 formed therearound to receive, turned thereover, a collar that is inwardly flared at 41. The collar flared portion 41 maintains the turning section collar 36 to sandwich the bearing 37 between the stationary sleeve top 15a and the turning section under surface 15a.

Shown in FIG. 1, a surgeon operator positions the guide 13 over a section of bone, with serrated edges 42 of that guide stationary sleeve end partially traveling into that bone mass. The guide is thereby securely positioned on that bone mass to allow the surgeon to turn drill 10, as described, into that bone mass. FIG. 7 shows a hole 45 that has been formed in the bone mass 44 by the process described above. The hole 45 is shown to include a surface portion 46 that conforms to the drill diameter of the fluted end 20. The hole is skirted outwardly at 47 as a result of the out travel of blade cutting edges 33a and 33b, that hole sloping inwardly from a greatest diameter at the skirt edge to the diameter of the drill shaft at the bone mass surface.

FIG. 8 shows a suture anchor applicator 50, hereinafter referred to as applicator, that includes a barrel 51 with an open end thereof that is shown positioned on bone mass 44 to be immediately opposite to the hole 45 that is shown in broken lines. The applicator 50, in addition to barrel 51, includes a spring housing 52 connected thereto that receives a plunger housing 53 telescoped therein that is for releasable connection to a plunger sleeve 54. The plunger sleeve 54, in turn, is maintained in a grip spring and plunger housing that is hereinafter referred to as grip 55, and includes a trigger 56 pivotally connected thereto at 57.

FIG. 9, is a longitudinal cross sectional view of the applicator 50 of FIG. 8 and shows that the barrel 51 and the housing 52 are preferably formed or connected together, as with the set screws or the like fastener arrangements, not shown, to form a single unit. Shown therein, the spring housing contains a coil spring 58 that is open longitudinally and is aligned with the longitudinal opening through barrel 51. The coil spring 58 is restrained on one end 58a in a depression 52a that is formed within the spring housing 52 to be approximately on line with the open barrel 51. The opposite coil spring end 58b is fitted into a depression 59a that is formed in a collar 59 of the plunger housing 53. So arranged, the plunger housing 53 can be moved longitudinally into the spring housing 52, compressing coil spring 58. Coil spring 58 thereby tends to return the plunger housing to the attitude shown in FIG. 9 when such compression force is removed therefrom, as will be explained later herein.

Shown also in FIG. 9 the plunger housing 53 receives, telescoped therein, the plunger sleeve 54 that is, in turn, turned at threads 54a into the grip 55. To retain the plunger sleeve 54 telescoped into the plunger housing 53, pins 60 are provided that extend at right or normal angles outwardly from that plunger sleeve to fit into guide slots 61 formed through the plunger housing 53. Shown in FIG. 8, each slot extends longitudinally from the plunger housing end and turns at a right angle at 61a to a lateral section. Pin 60 is fitted into slot 61 to travel therealong to right angle 61a whereat, by turning that plunger sleeve relative to the housing, pin 60 travels into the slot lateral section, providing a locking of the plunger sleeve to the plunger housing. This locking is maintained after an anchor ejector 70 is fitted therein, as will be described later herein with respect to a discussion of FIGS. 10 and 11.

As set out above, the plunger sleeve 54 is secured to the grip 55 by turning plunger sleeve threads 54a into like threads cut into in the longitudinal opening of chamber 62 that is formed in that grip. Shown in FIG. 9, that longitudinal opening is stepped downwardly from the threaded portion into a spring chamber wherein is longitudinally contained a coil spring 63. The coil spring ends are maintained between a further stepped down portion 64 of that grip chamber, the opposite spring end 63b butting into a shoulder 65a of a piston 65.

Piston 65 at shoulder 65a, as shown in FIG. 9, is stepped down to a section 66 that extends through a rearward facing opening in the grip 55 to terminate in a pivot end 67 whereto trigger 56 is pivotally coupled at pin 68. So arranged, as illustrated in FIG. 8, a surgeon operator holding the finger engaging portions 55a of grip 55, depressing the trigger 56 with the heal of his hand will move the piston 65 against the biasing of spring 63. The piston 65, on the opposite end to the pivot coupling to trigger 56 includes a yoke coupling 69 arranged to travel along the inner surface of the piston sleeve 54 when the piston is moved. So arranged, pressing of the trigger 56 moves the piston 65 and its yoke coupling 69 rearwardly towards the trigger. The yoke coupling 69, as shown best in FIG. 9, can receive as shown best in FIGS. 10 and 11, a mandrel head 71 fitted therein, hereinafter referred to as mandrel head 71, which mandrel head is part of ejector 70. The mandrel head 71 is an end of an anchor mandrel 72 that is telescoped into a longitudinal opening through an ejector housing 73 of ejector 70, hereinafter referred to as ejector sleeve 73. The ejector sleeve 73 extends from a head end 74 thereof that is for arrangement, as shown in FIG. 9, within the plunger housing to fit between the yoke coupling 69 of the plunger and plunger housing collar 59. The ejector sleeve mounts on its opposite end, a slotted ring 76 and an anchor rivet 75, that is shown to have somewhat of an acorn shape. The slotted ring 76 is arranged to fracture strategically at slots 87 formed in spaced apart relationship therearound, which ring fracturing and the resultant anchor rivet locking therein will be described in detail later herein with respect to the functioning of the anchor mandrel 70.

FIGS. 10 and 11 show the ejector 70 removed from its contained attitude in the barrel 51 and spring housing 52 of the applicator 50. By appropriately twisting the plunger housing 53 to effect rotation of that sleeve with respect to that plunger sleeve 54 the pins 60 extending therefrom are displaced from slots 61. This allows the applicator to be broken apart, the plunger 65 and plunger sleeve 54 telescoping out of engagement from within the plunger housing 53, exposing the plunger yoke coupling 69. So arranged, mandrel head 71 of anchor ejector 70 can be fitted into and removed from yoke coupling 69. In practice therefore, the ejector 70 can easily be installed and removed from the applicator 50 by merely turning the plunger housing 53 relative to the plunger sleeve 54 and withdrawing the connected anchor ejector 70 therefrom. After use, to reload the assembly a new anchor ejector 70 can be installed by fitting its mandrel head to the plunger yoke and refitting the ejector into the spring housing 52 so that it extends longitudinally therethrough and through the coil spring 58 and barrel 51, as shown in FIG. 9.

FIG. 10 shows the anchor ejector 70 essentially as it would appear mounted in applicator 50 of FIGS. 8 and 9. The anchor ejector consists of the ejector sleeve 73 that is open longitudinally at 77 from end and end to receive the anchor mandrel 72 telescoped longitudinally therethrough. The anchor mandrel terminates on one end in mandrel head 71 and fits through the sloted ring 76 on its other end to releasably connect by turning it into the anchor rivet 75. The anchor mandrel 72 is arranged to slide freely back and forth in the longitudinal opening 77 through the ejector sleeve 73. So arranged, movement of the mandrel head 71 away from the ejector collar 74, as illustrated in FIG. 11, draws the anchor mandrel along that longitudinal opening 77. As the anchor mandrel is so moved, the anchor rivet 75 connected to threaded end 83 thereof will be drawn therewith into slotted ring 76. The anchor rivet 75 is formed to have a somewhat acorn shape including a forward sloping nose end 78 that terminates, medial therearound, in a ridge 79. Proceeding along the anchor rivet from sloping nose end 78 and ridge 79 the anchor rivet includes a groove 80. The slotted ring 76, to receive the anchor rivet sloping end 78, includes an outwardly sloped surface 81 that terminates at a sharp edge 81a followed by, medial therein, a groove 82. Groove 82 is shaped to receive the anchor ridge 79 fitted therein. As the anchor rivet 75 enters slotted ring 76 the sloping nose end 78 of that anchor rivet slides along the outwardly sloped surface 81 of that ring, causing the ring to break at slots 87 forming ring sections that flare outwardly, as illustrated in FIG. 12. The ring thereby expands to the attitude shown in FIG. 11 as the anchor rivet travels therein. With continued travel of the anchor rivet into ring 76 the anchor ridge 79 will align with and seat in the ring groove 82 that is formed within the slotted ring around the circumference thereof. With the anchor rivet ridge 79 seated in the ring groove 82, the ring sharp edge 81a, will rest in the anchor groove 80. This arrangement provides two points of locking to hold the anchor rivet and slotted ring together as the suture anchor, as shown in FIG. 11.

As the applicator 50 is actuated the anchor mandrel at head 71 moves rearwardly pulling the anchor rivet 75 into the slotted ring 76, forming the suture anchor. Thereafter, with continued travel of the mandrel head threads at the mandrel end 83 that are turned into first flights of threads formed in a rivet longitudinal passage 84 of the rivet 75 will fail the mandrel end pulling out of engagement with that anchor rivet end passage 84. The anchor rivet 75 is thereby separated from the anchor mandrel, as shown in FIG. 11. In which separation a suture 85 connected to the suture anchor will be drawn out of the anchor mandrel. The suture, as shown best in FIG. 10, extends through the anchor rivet longitudinal passage 84 wherein the mandrel end 83 is turned, and is threaded through at intersecting lateral passage 84a or 84b, across the anchor rivet head 86 and back into longitudinal passage 84 through the other lateral passage 84a or 84b. Which lateral passages 84a and 84b intersects anchor passage 84 at right angles. The suture 85 is a continuous strand that is threaded over the anchor head end 86 and is thereby maintained to extend from the anchor rivet as two strands without necessitating knotting or having that suture exposed to a sharp edge as at the junctions of holes 84a and 84b with opening 84 as could cut that suture.

FIG. 11 shows the suture being drawn out of the anchor mandrel 72 after separation from the anchor rivet 75. The anchor mandrel is drawn therefrom until it can be removed from the suture as illustrated in FIG. 12. FIG. 12, of course, shows the same view of a section of bone mass 44 as is shown in FIG. 7. Hole 45 should be taken as having preferably been formed by the operation of the drill 10 of the present invention and FIG. 12 shows the anchor rivet 75 locked in the slotted ring 76, as the suture anchor where the slotted ring end has expanded to fll the skirt portion 47 of the hole 45. A permanent locking together of the anchor rivet and slotted ring into the suture anchor of the invention is thereby provided. In which arrangement the slotted ring has expanded to where its greatest diameter is greater than the diameter of hole 45 at the bone mass 44 surface. Thereby, absent breaking of the bone mass around the hole 45, the suture anchor cannot be withdrawn from the hole 45. The positive locking of the anchor rivet in the slotted ring within that bone mass has been found in practice to be stronger in tensil strength than is the suture 85. The suture 85 will therefore tend to break before the suture anchor will fracture out of the bone mass 44 around hole 45.

It is well known in the field of orthopaedic medicine that a bone mass within a fairly short period of time, usually within six (6) to fourteen (14) weeks, will fill in a drilled opening with tissue. It is preferred to form the anchor rivet and slotted ring of the present invention from a plastic such as a polylactic acid that is bio-degradable within the body. Such plastic suture anchor and suture will thereby be dissolved and absorbed by the body after the healing process is completed. In such healing process, a ligament secured to that bone mass by that suture will have grown to the bone and with the dissolving of the suture and suture anchor the drilled hole will fill with tissue, the bone mass eventually appearing as if no procedure has been performed thereat. While a polylactic acid plastic is preferred, it should be understood that the anchor rivet and slotted ring of the present invention, within the scope of this disclosure, can be manufactured from any material whether it be bio-degradable or not. Except, of course, if a medal is used in their construction the suture anchor will remain in the bone mass unless and until it is physically removed after the procedure. Such metal should be sufficiently ductile to break along the splits or slots in the slotted ring and should tend to return or spring back to its original round configuration with the anchor rivet installed therein so as to maintain the anchor rivet ridge 79 in slotted ring groove 82.

A practice of the present invention therefore involves, as illustrated first in FIG. 1, the location by a surgeon of a preferred or desired location on a bone mass 44 for attaching or securing a suture anchor with a suture extended therefrom. FIG. 1 illustrates the surgeon holding the guide 13 such that the serrated edge 42 of guide stationary sleeve 15 engages and even bites into the bone mass. Thereafter, the drill 10 of the invention mounted in a chuck 12 is installed in that guide so that the drill fluted end 20 is fitted through the guide 13. The drill fluted end is turned into the bone mass to a depth where an end 19a of the drill lower guide sleeve 19 engages a stepped portion 35 arranged within and across the turning sleeve 14. Thereat, the surgeon operator pushing the drill 10 further into the bone mass and guide 13 causes the lower guide sleeve 19 to travel up the drill shaft, that lower guide sleeve interior riding along and up slides or ramps 32a and 32b of pivoting blades 24a and 24b. The blades are thereby closed together at the ramp ends, the opposite blade ends pivoting outwardly around sissor pivot 23 to the attitude shown in FIG. 3. This blade sissoring occurs as the fluted drill end penetrates the bone mass and travels therein. Within the bone mass the cutting blade edges 33a and 33b of the pivoting blades 24a and 24b extend outwardly to cut a skirted hole in the bone mass that is like the hole 45 shown in FIG. 7. Such drilling continues until sleeve 19 engages and is stopped by flat surfaces 34a and 34b of sissoring blade ends 31a and 31b, as illustrated in FIG. 4. In which attitude the blade cutting edges 33a and 33b will have been moved outwardly to their fully extended attitude. Thereafter, withdrawal of the drill from the hole, as illustrated in FIG. 4, allows the spring 28, as illustrated in FIG. 2, to bias the connected upper and lower guide sleeves towards the drill fluted end 20. The blades 24a and 24b are thereby pivoted back together to the attitude shown in FIG. 2 as the drill 10 is removed from the drilled hole without disrupting the opening at the bone mass surface.

To attach the suture anchor in the drilled hole 45, the surgeon, after removal of the guide and drill and cleaning out of the hole, positions the applicator 50 thereover as illustrated in FIG. 8. In such positioning the applicator barrel 51 end wherein the anchor rivet and slotted ring are maintained is positioned over the hole 45. The surgeon will have previously locked together the plunger housing and plunger sleeve thereby placing the anchor rivet 75 in slotted ring 76 in tension with the anchor rivet 75 somewhat drawn into the slotted ring 76 to maintain a tight coupling therebetween. With the positioning of the barrel 51 of applicator 50 over the area surrounding the hole 45, a surgeon operator holding the applicator at grip 55 with the palm of his hand over and around trigger 56 applies pressure thereon as would move the applicator towards that bone mass. The barrel 51 moves in opposition to the spring biasing of coil spring 58 uncovering and allowing the anchor rivet 75 and slotted ring 76 to travel into that flared opening 45. Thereafter, with an application of force to trigger 57 that pivots it around pivot 56 towards grip 55, the piston or plunger yoke 69 will move away from hole 45. That trigger rotation and plunger and yoke movement draws the connected mandrel head 71 therewith. As shown in FIG. 11, anchor mandrel 72 that mounts rivet anchor 75 is thereby being drawn into slotted ring 76. The slotted ring 76 is split along slots 87 by that travel of rivet anchor therein until an anchor ridge 79 fits into a slot 82 formed around the inside circumference of that slotted ring. This is the attitude of the suture anchor shown in FIG. 11. Therein, the mandrel body is shown as having separated from the anchor rivet and is being drawn therefrom so as to expose the suture 85 extending from the suture anchor. Continued withdrawal of the applicator 50 away from the anchor rivet and slotted ring draws the suture 85 out of the longitudinal opening 77 in mandrel 72, leaving it exposed as illustrated in FIG. 12. Whereafter, the surgeon using the two ends of that suture can attach a ligament thereto, drawing it tightly against that bone mass where it remains during the healing process.

With the removal of the suture from the anchor mandrel 72 the ejector 70 is empty and can be replaced with a filled ejector by a surgeon. In such replacement the surgeon holds the grip 55 or the plunger sleeve 54 and turns the plunger housing 53 such that the pins 60 in the plunger sleeve move appropriately within slot 61 of the plunger housing. The plunger sleeve and housing are thereby disconnected and can be separated. The mandrel head of the used ejector 70 can then be removed from plunger yoke 69 and discarded. A new ejector 70 can then be installed, the mandrel head fitted to the plunger yoke, and the barrel 51 and spring housing 52 fitted thereover with the plunger housing 53 reconnected to the plunger sleeve 54. In which separation and reinstallation of the plunger housing to the plunger sleeve it has found to be helpful to take up spring tension in plunger spring 63 by slightly pressing trigger 56 such that plunger sleeve and plunger housing can be easily telescoped together, which movement of trigger 56 should just be sufficient to allow for the coupling of these components.

While the preferred embodiment of our invention in a suture anchor system has been shown and described herein, it should be understood that the disclosure is made by way of example only and that variations are possible to the structure of the invention and its use without departing from the subject matter coming within the scope of the following claims, which claims we regard as our invention.

We claim:

1. A suture anchor system comprising a drill means for forming a hole in a bone mass that has an internal diameter that is greater than the diameter of the hole entry; a suture anchor applicator for fitting and expanding a suture anchor whereto a suture is connected into a hole formed by operation of said drill means, which suture anchor includes an anchor rivet whereto said suture is attached and a slotted ring arranged to receive said anchor rivet moved therein so as to fracture that ring along slots formed therein, flaring the ring outwardly into a skirt, the anchor rivet locking thereto forming the suture anchor; means for maintaining said anchor rivet and slotted ring in said hole while said anchor rivet is drawn into said slotted ring; and means for drawing said anchor rivet into said slotted ring to where said anchor rivet and slotted ring couple together into said suture anchor, which drawing means includes a mandrel having means for releasable connection to said anchor rivet whereby, with an application of a certain pulling force where said anchor rivet is seated in said slotted ring, said mandrel means will release from said anchor rivet, exposing said suture secured to that suture anchor.

2. A suture anchor system as recited in claim 1, wherein the drill means includes a drill that incorporates a straight shaft for fitting at one end into a turning means and has a fluted cutting end distal therefrom with said shaft adjacent to the distal end incorporating a longitudinal slot formed therethrough wherein a pair of scissor blades are pivotally connected at mid points of each, which blades are identical and face oppositely to scissor apart and include cutting edges formed in the blade ends near the shaft fluted end and a ramp means formed proximate to each blade end distal therefrom, the blade ramps to extend oppositely beyond the shaft when said blade cutting edges are closed within said shaft slot, said scissor blades further including stops on the distal ends from the cutting edges, the stops to extend outwardly and include right angle faces to the drill shaft; and a sleeve means telescoped over said drill shaft to move back and forth over said drill shaft longitudinal slot portion containing said blade ramps.

3. A suture anchor system as recited in claim 2, further including slots formed in the sleeve means, each slot to align with and receive and pass therethrough, respectively, each sissor blade ramp and stop, each slot end closest to the drill shaft fluted end to travel up a said blade ramp, the slot end urging the ramps together, thereby extending said blade stops until the right angle faces of said stops butt against to block further travel of said sleeve means away from said drill shaft fluted end.

4. A suture anchor system as recited in claim 2, further including means for moving the sleeve means over said blade ramps consisting of a cylinder that receives the drill shaft fluted end therethrough to engage, as said drill end is passed therethrough, said sleeve means to urge it along and over the blade ramps, said guide means cylinder including a fixed section for stationary engagement with a point of a bone mass and a turning section that includes a means for engaging and turning with said sleeve means.

5. A suture anchor system as recited in claim 4, wherein the guide means cylinder fixed section includes an open sleeve that has a serrated edge around one end thereof for engaging a bone mass surface and connects to a handle means for holding by a surgeon operator to position the sleeve serrated edge on said bone mass, and the turning section is an open sleeve that is bearing coupled to said fixed sleeve and includes a step therein of a diameter to pass the drill shaft fluted end therethrough that engages the end of said sleeve means.

6. A suture anchor system as recited in claim 2, further including means for biasing said sleeve means out of engagement with said blade ramps to cause said blades to scissor together to where said blade cutting edges are recessed into said drill shaft slot that is a coil spring contained within a housing that is fixed to the drill shaft that is telescoped therethrough said housing is arranged to receive the sleeve means in sliding engagement telescoped therein containing said coil spring end.

7. A suture anchor system as recited in claim 1, wherein the applicator incorporates a grip means for holding by a surgeon operator that includes a trigger means pivotally connected thereto for operation by that surgeon operator to move a plunger portion towards the surgeon operator holding said grip means; the means for maintaining the anchor rivet and slotted ring in the hole is a barrel that is releasably connected to said grip means and is open longitudinally to accommodate an ejector telescoped therethrough that includes the mandrel telescoped therethrough; and means for coupling said mandrel drawing end distal from its anchor rivet coupling to said plunger portion, said plunger portion providing the means for drawing said anchor rivet into said slotted ring.

8. A suture anchor system as recited in claim 7, wherein the grip means includes the plunger portion fitted therethrough that is telescoped through a spring means in said grip means for biasing that plunger portion towards the barrel away from the surgeon operator; and the trigger pivotal connection to said grip means is such that, when said trigger is depressed towards said grip means, said plunger portion connected thereto will be moved against said spring biasing.

9. A suture anchor system as recited in claim 7, wherein the means for coupling the mandrel means to said plunger portion includes a head formed across the mandrel end distal from the anchor rivet for releasably fitting into a yoke means secured to the plunger portion end opposite to its coupling to the trigger.

10. A suture anchor system as recited in claim 7, wherein the means for releasably coupling said grip means and barrel includes a plunger sleeve that is secured to said grip means and is open longitudinally to receive the plunger portion telescoped therethrough; a plunger housing for telescoping over and releasable coupling to said plunger sleeve; a spring housing as part of the barrel that contains a coil spring open longitudinally therethrough, which opening is aligned with said barrel longitudinal opening, said spring housing to receive said plunger housing end telescoped therein against the biasing of said coil spring; and means for releasably securing said plunger housing in telescoped connection over said plunger sleeve.

11. A suture anchor system as recited in claim 10, wherein the barrel spring housing is flanged inwardly and the plunger housing end that is telescoped therein is flanged outwardly, the flange faces to butt against one another blocking travel of the plunger housing out of the barrel spring housing responsive to the biasing of the coil spring.

12. A suture anchor system as recited in claim 10, wherein the means for releasably securing said plunger housing in telescoping connection over said plunger sleeve consists of a pin that projects outwardly at a right angle from said plunger sleeve; and a slot formed in said plunger housing to receive said pin slidably fitted therein, said slot to extend longitudinally from the plunger housing end to a right angle bend and thence a lateral distance therefrom.

13. A suture anchor system as recited in claim 7, wherein the ejector is arranged to telescope within and slide freely through the barrel and consists of an ejector sleeve that has a collar formed on one end thereof that has approximately the diameter of the plunger sleeve, which ejector sleeve is open longitudinally to receive the mandrel fitted in sliding engagement therethrough.

14. A suture anchor system as recited in claim 13, wherein the ejector sleeve has approximately the same diameter as does the slotted ring; and the mandrel threaded end opposite to the head end is fitted through said slotted ring and is turned into said anchor rivet.

15. A suture anchor system as recited in claim 1, wherein the slotted ring is sloped outwardly on one end from its inner surface to its outer surface forming a sharp edge at its outer diameter and includes a medial groove formed around the ring inner surface; and the anchor rivet has a tapered nose end to travel along said slotted ring sloped end to break the ring at the slots, outwardly flaring that slotted ring end, the anchor tapered end terminating in a ridge, which ridge will fit in locking engagement into said slotted ring medial groove.

16. A suture anchor system as recited in claim 15, further including a groove formed around the anchor rivet surface, adjacent to the ridge, to receive, in locking engagement, a slotted ring lip end located between the groove and the slotted ring end at the junction with the outward sloping surface.

17. A suture anchor system as recited in claim 15, further including a longitudinal hole formed through the anchor rivet to receive a suture threaded therethrough; and a longitudinal opening through the mandrel to receive said suture therethrough that is threaded to receive the mandrel threaded end turned therein.

18. A suture anchor system as recited in claim 17, further including a lateral hole formed through the anchor rivet that intersects the longitudinal hole at approximately a right angle, the suture to be threaded into the longitudinal hole at the tapered nose and out one end of the lateral hole, then across the anchor rivet head end, and back through the other end of the lateral passage into the longitudinal passage and out the anchor rivet nose end, providing a two strand suture that is fitted through the mandrel means longitudinal passage.

19. A suture anchor system as recited in claim 15, wherein the slotted ring has a plurality of spaced apart longitudinal slots formed therein from the sloping end.

20. A suture anchor system as recited in claim 1, wherein the anchor rivet and slotted ring are formed out of bio-degradable material to be absorbed by the body along with the suture after the body healing process is completed.

21. A suture anchor system as recited in claim 20, wherein the anchor rivet and slotted ring are formed of polylactic acid plastic.

22. A suture anchor system as recited in claim 1, wherein the mandrel releasable connection means consists of shallow threads formed in a mandrel end opposite to a drawing distal end thereof, which shallow threads are for turning into a threaded cavity formed in said anchor rivet end, the mandrel end threads to pull out from said anchor rivet end after said anchor rivet has seated in said slotted ring.

23. A suture anchor applicator for fitting and expanding an anchor means whereto a suture is connected into a hole formed in a bone mass to have a greater sub-surface diameter than the hole diameter at the bone mass surface comprising, a suture anchor that includes an anchor rivet whereto said suture is attached and a slotted ring arranged to receive said anchor rivet moved therein so as to fracture that ring along slots formed therein that extend longitudinally from a leading edge, flaring the ring outwardly into a skirt; means for locking said anchor rivet in said slotted ring forming a suture anchor; means for maintaining said anchor rivet and slotted ring in said hole while said anchor rivet is drawn into said slotted ring; and means for drawing said anchor rivet into said slotted ring to where said anchor rivet and slotted ring will couple together into said suture anchor, which drawing means includes a mandrel having means for releasable connection to said anchor rivet whereby, on application of a certain pulling force where said anchor rivet is seated in said slotted ring, said mandrel means will release from said anchor rivet, exposing said suture secured to that suture anchor.

24. A suture anchor applicator as recited in claim 23, wherein the applicator incorporates a grip means for holding by a surgeon operator that includes a trigger means pivotally connected thereto for operation by that surgeon operator to move a plunger portion towards the surgeon operator holding said grip means; the means for maintaining the anchor rivet and slotted ring in the hole is a barrel that is releasably connected to said grip means and is open longitudinally to accommodate an ejector telescoped therethrough that includes the mandrel telescoped therethrough; and means for coupling said mandrel drawing end distal from its anchor rivet coupling to said plunger portion, said plunger portion providing the means for drawing said anchor rivet into said slotted ring.

25. A suture anchor applicator as recited in claim 24, wherein the grip means includes the plunger portion fitted therethrough that is telescoped through a spring means in said grip means for biasing that plunger portion towards the barrel away from the surgeon operator; and the trigger pivotal conection to said grip means is such that, when said trigger is depressed towards said grip means, said plunger portion connected thereto will be moved against said spring biasing.

26. A suture anchor applicator as recited in claim 24, wherein the means for coupling the mandrel means to said plunger portion includes a head formed across the mandrel end distal from the anchor rivet for releasably fitting into a yoke means secured to the plunger portion end opposite to its coupling to the trigger.

27. A suture anchor applicator as recited in claim 24, wherein the means for releasably coupling said grip means and barrel includes a plunger sleeve that is secured to said grip means and is open longitudinally to receive the plunger portion telescoped therethrough; a plunger housing for telescoping over and releasable coupling to said plunger sleeve; a spring housing as part of the barrel that contains a coil spring open longitudinally therethrough, which opening is aligned with said barrel longitudinal opening, said spring housing to receive said plunger housing end telescoped therein against the biasing of said coil spring; and means for releasably securing said plunger housing in telescoped connection over said plunger sleeve.

28. A suture anchor applicator as recited in claim 27, wherein the barrel spring housing is flanged inwardly and the plunger housing end that is telescoped therein is flanged outwardly, the flange faces to butt against one another blocking travel of the plunger housing out of the barrel spring housing responsive to the biasing of the coil spring.

29. A suture anchor applicator as recited in claim 27, wherein the means for releasably securing said plunger housing in telescoping connection over said plunger sleeve consists of a pin that projects outwardly at a right angle from said plunger sleeve; and a slot formed in said plunger housing to receive said pin slidably fitted therein, said slot to extend longitudinally from the plunger housing end to a right angle bend and thence a lateral distance therefrom.

30. A suture anchor applicator as recited in claim 24, wherein the ejector is arranged to telescope within and slide freely through the barrel and consists of an ejector sleeve that has a collar formed on one end thereof that has approximately the diameter of the plunger sleeve, which ejector sleeve is open longitudinally to receive the mandrel fitted in sliding engagement therethrough.

31. A suture anchor applicator as recited in claim 30, wherein the ejector sleeve has approximately the same diameter as does the slotted ring; and the mandrel threaded end opposite to the head end is fitted through said slotted ring and is turned into said anchor rivet.

32. A suture anchor applicator as recited in claim 23, wherein the mandrel releasable connection means consists of shallow threads formed in a mandrel end thereof opposite to a drawing end thereof, which threads are shallow and are for turning into a threaded cavity formed in said anchor rivet end, the mandrel end threads to pull out from said anchor rivet end after said anchor rivet has seated in said slotted ring.

33. A suture anchor comprising, an anchor rivet whereto said suture is attached and a slotted ring arranged to receive said anchor rivet moved therein so as to fracture that ring along slots formed therein, flaring the ring outwardly into a skirt; means for locking the anchor rivet in said slotted ring forming the suture anchor; means for maintaining said anchor rivet and slotted ring in a hole in a bone mass prepared to receive the suture anchor in right fitting engagement while said anchor rivet is drawn into said slotted ring; and means for drawing said anchor rivet into said slotted ring to where said anchor rivet and slotted ring couple together into said suture anchor, which drawings means includes a mandrel having means for releasable connection to said anchor rivet whereby, on application of a certain pulling force where said anchor rivet is seated in said slotted ring, said mandrel means will release from said anchor rivet, exposing said suture anchor.

34. A suture anchor as recited in claim 33, wherein the slotted ring is sloped outwardly on one end from its inner surface to its outer surface forming a sharp edge at its outer diameter and includes a medial groove formed around the ring inner surface; and the anchor rivet has a tapered nose end to travel along said slotted ring sloped end to break the ring at the slots, outwardly flaring that slotted ring end to fill the hole in the bone mass, the anchor tapered end terminating in a ridge, which ridge will fit in locking engagement into said slotted ring medial groove.

35. A suture anchor as recited in claim 34, further including a groove formed around the anchor rivet surface, adjacent to the ridge, to receive, in locking engagement, a slotted ring lip end located between the groove and the slotted ring end at the junction with the outward sloping surface.

36. A suture anchor as recited in claim 34, further including a longitudinal hole formed through the anchor rivet to receive a suture threaded therethrough; and a longitudinal opening through the mandrel to receive said suture therethrough that is threaded to receive the mandrel threaded end turned therein.

37. A suture anchor as recited in claim 36, further including a lateral hole formed through the anchor rivet that intersects the longitudinal hole at approximately a right angle, the suture to be threaded into the longitudinal hole at the tapered nose and out one end of the lateral hole, then across the anchor rivet head end and back through the other end, of the lateral passage into the longitudinal passage and out the anchor rivet nose end, providing a two strand suture that is fitted through the mandrel means longitudinal passage.

38. A suture anchor as recited in claim 34, wherein the slotted ring has a plurality of spaced apart longitudinal slots formed therein from the sloping end.

39. A suture anchor as recited in claim 33, wherein the anchor rivet and slotted ring are formed out of bio-degradable material to be absorbed by the body along with the suture after the body healing process is completed.

40. A suture anchor as recited in claim 39, wherein the anchor rivet and slotted ring are formed of polylactic acid plastic.

41. A suture anchor as recited in claim 33, wherein the mandrel releasable connection means consists of shallow threads formed in a mandrel end opposite to a drawing distal end thereof, which shallow threads are for turning into a threaded cavity formed in said anchor rivet end, the mandrel end threads to pull out from said anchor rivet end after said anchor rivet has seated in said slotted ring.

* * * * *